US009713522B2

(12) United States Patent
Gill et al.

(10) Patent No.: US 9,713,522 B2
(45) Date of Patent: Jul. 25, 2017

(54) ESOPHAGEAL STENT WITH VALVE

(71) Applicant: Merit Medical Systems, Inc., South Jordan, UT (US)

(72) Inventors: Darla Gill, Salt Lake, UT (US); Zeke Eller, Plano, TX (US); Rich Snider, Dallas, TX (US); Trent Clegg, Camarillo, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 14/661,562

(22) Filed: Mar. 18, 2015

(65) Prior Publication Data

US 2015/0190220 A1    Jul. 9, 2015

Related U.S. Application Data

(63) Continuation of application No. 13/285,358, filed on Oct. 31, 2011, now Pat. No. 8,986,368.

(51) Int. Cl.
| | | |
|---|---|---|
| *A61F 2/04* | (2013.01) | |
| *A61F 2/24* | (2006.01) | |
| *A61F 2/915* | (2013.01) | |
| *A61F 2/07* | (2013.01) | |

(52) U.S. Cl.
CPC ....... *A61F 2/04* (2013.01); *A61F 2/07* (2013.01); *A61F 2/24* (2013.01); *A61F 2/915* (2013.01); *A61F 2002/044* (2013.01); *A61F 2002/91575* (2013.01); *A61F 2220/0008* (2013.01)

(58) Field of Classification Search
CPC ................................. A61F 2/06; A61M 29/00

USPC ........... 623/1.1–1.2, 1.49–1.54, 23.7, 23.71; 606/191–197
See application file for complete search history.

(56) References Cited

U.S. PATENT DOCUMENTS

| | | | |
|---|---|---|---|
| 5,061,275 | A | 10/1991 | Wallsten et al. |
| 5,152,797 | A | 10/1992 | Luckman et al. |
| 5,314,473 | A | 5/1994 | Godin |
| 5,607,445 | A | 3/1997 | Summers |
| 5,662,713 | A | 9/1997 | Andersen et al. |
| 5,833,707 | A | 11/1998 | McIntyre et al. |
| 5,843,175 | A | 12/1998 | Frantzen |
| 5,855,600 | A | 1/1999 | Alt |
| 6,221,091 | B1 | 4/2001 | Khosravi |
| 6,254,642 | B1 | 7/2001 | Taylor |

(Continued)

FOREIGN PATENT DOCUMENTS

| | | |
|---|---|---|
| CN | 1433818 A | 8/2003 |
| CN | 201200504 Y | 3/2009 |

(Continued)

OTHER PUBLICATIONS

European Search Report dated Feb. 18, 2015 for EP12793791.0.

(Continued)

*Primary Examiner* — Yashita Sharma
(74) *Attorney, Agent, or Firm* — Stoel Rives LLP

(57) ABSTRACT

A stent comprised of a valve and a scaffolding structure having components configured to allow at least a portion of the stent to decrease in diameter in response to an axial force applied to the stent. Further, the components and elements of the stent may be configured to balance transverse forces applied to the stent, thus reducing the incidence of infolding.

20 Claims, 9 Drawing Sheets

(56) References Cited

U.S. PATENT DOCUMENTS

| | | |
|---|---|---|
| 6,264,700 B1 | 7/2001 | Kilcoyne et al. |
| 6,302,917 B1 | 10/2001 | Dua et al. |
| 6,348,065 B1 | 2/2002 | Brown et al. |
| 6,464,720 B2 | 10/2002 | Boatman et al. |
| 6,511,505 B2 | 1/2003 | Cox et al. |
| 6,544,291 B2 | 4/2003 | Taylor |
| 6,635,082 B1 | 10/2003 | Hossainy et al. |
| 6,669,724 B2 | 12/2003 | Park et al. |
| 6,764,518 B2 | 7/2004 | Godin |
| 6,845,776 B2 | 1/2005 | Stack et al. |
| 6,878,162 B2 | 4/2005 | Bales et al. |
| 6,913,619 B2 | 7/2005 | Brown et al. |
| 6,929,658 B1 | 8/2005 | Freidberg et al. |
| 6,991,647 B2 | 1/2006 | Jadhav |
| 7,182,788 B2 | 2/2007 | Jung et al. |
| 7,462,192 B2 | 12/2008 | Norton et al. |
| 7,547,321 B2 | 6/2009 | Silvestri et al. |
| 7,637,942 B2 | 12/2009 | Mangiardi et al. |
| 7,695,446 B2 | 4/2010 | Levine et al. |
| 7,722,624 B2 | 5/2010 | Boucher et al. |
| 8,114,045 B2 | 2/2012 | Surti |
| 8,500,821 B2 | 8/2013 | Sobrino-Serrano et al. |
| 8,523,936 B2 | 9/2013 | Schmid et al. |
| 8,986,368 B2 | 3/2015 | Gill et al. |
| 2002/0032479 A1 | 3/2002 | Hankh et al. |
| 2002/0068967 A1 | 6/2002 | Drasler et al. |
| 2002/0107565 A1 | 8/2002 | Greenhalgh |
| 2002/0116052 A1 | 8/2002 | Cox et al. |
| 2002/0138135 A1 | 9/2002 | Duerig et al. |
| 2003/0009236 A1 | 1/2003 | Godin |
| 2004/0019374 A1 | 1/2004 | Hojeibane et al. |
| 2004/0044396 A1 | 3/2004 | Clerc et al. |
| 2004/0044401 A1 | 3/2004 | Bales et al. |
| 2004/0088040 A1 | 5/2004 | Mangiardi et al. |
| 2004/0107004 A1 | 6/2004 | Levine et al. |
| 2004/0116996 A1 | 6/2004 | Freitag |
| 2004/0127973 A1 | 7/2004 | Mangiardi et al. |
| 2004/0204749 A1 | 10/2004 | Gunderson |
| 2004/0267350 A1* | 12/2004 | Roubin ............... A61F 2/91 623/1.13 |
| 2005/0080491 A1 | 4/2005 | Levine et al. |
| 2006/0122686 A1 | 6/2006 | Gilad et al. |
| 2006/0122692 A1 | 6/2006 | Gilad et al. |
| 2006/0212052 A1 | 9/2006 | Shin et al. |
| 2006/0253190 A1 | 11/2006 | Kuo |
| 2006/0259137 A1 | 11/2006 | Artof et al. |
| 2006/0276874 A1 | 12/2006 | Wilson et al. |
| 2007/0038290 A1 | 2/2007 | Huang et al. |
| 2007/0050011 A1 | 3/2007 | Klein et al. |
| 2007/0050021 A1 | 3/2007 | Johnson |
| 2007/0100437 A1 | 5/2007 | Welborn et al. |
| 2007/0112437 A1 | 5/2007 | Shank |
| 2007/0150049 A1 | 6/2007 | Nissl |
| 2007/0198097 A1 | 8/2007 | Zegdi |
| 2007/0239273 A1 | 10/2007 | Allen |
| 2007/0276463 A1 | 11/2007 | Nissl et al. |
| 2008/0004688 A1 | 1/2008 | Spenser et al. |
| 2008/0097579 A1 | 4/2008 | Shanley et al. |
| 2008/0132998 A1 | 6/2008 | Mangiardi et al. |
| 2008/0140181 A1 | 6/2008 | Reynolds et al. |
| 2008/0154351 A1 | 6/2008 | Leewood et al. |
| 2008/0200979 A1 | 8/2008 | Dieck et al. |
| 2008/0221664 A1 | 9/2008 | Bales et al. |
| 2008/0221670 A1 | 9/2008 | Clerc |
| 2008/0243225 A1 | 10/2008 | Satasiya et al. |
| 2008/0288044 A1 | 11/2008 | Osborne |
| 2009/0036976 A1 | 2/2009 | Beach et al. |
| 2009/0043373 A1 | 2/2009 | Arnault De La Menardiere et al. |
| 2009/0105809 A1 | 4/2009 | Lee et al. |
| 2009/0171456 A1* | 7/2009 | Kveen ............... A61F 2/2418 623/2.11 |
| 2009/0171465 A1 | 7/2009 | Bucay-Couto et al. |
| 2009/0187240 A1 | 7/2009 | Clerc |
| 2010/0004728 A1 | 1/2010 | Rao et al. |
| 2010/0036504 A1 | 2/2010 | Sobrino-Serrano et al. |
| 2010/0049313 A1 | 2/2010 | Alon et al. |
| 2010/0082093 A1 | 4/2010 | Weber |
| 2010/0114327 A1 | 5/2010 | Sobrino-Serrano et al. |
| 2010/0121461 A1 | 5/2010 | Sobrino-Serrano et al. |
| 2010/0121462 A1 | 5/2010 | Sobrino-Serrano et al. |
| 2010/0137998 A1 | 6/2010 | Sobrino-Serrano et al. |
| 2010/0173066 A1 | 7/2010 | Mangiardi et al. |
| 2010/0256744 A1 | 10/2010 | Laborde et al. |
| 2010/0286760 A1 | 11/2010 | Beach et al. |
| 2011/0004290 A1 | 1/2011 | Bales, Jr. et al. |
| 2011/0054592 A1 | 3/2011 | Fliedner |
| 2011/0160836 A1 | 6/2011 | Behan |
| 2011/0190874 A1 | 8/2011 | Celermajer et al. |
| 2011/0190905 A1 | 8/2011 | Behan |
| 2011/0265908 A1 | 11/2011 | Clerc |
| 2011/0319980 A1 | 12/2011 | Ryan |
| 2012/0010697 A1 | 1/2012 | Shin et al. |
| 2012/0059486 A1 | 3/2012 | Sobrino-Serrano et al. |
| 2012/0071987 A1 | 3/2012 | Levy |
| 2013/0006382 A1 | 1/2013 | Behan |
| 2013/0103163 A1 | 4/2013 | Krimsky et al. |

FOREIGN PATENT DOCUMENTS

| | | |
|---|---|---|
| CN | 104114201 A | 10/2014 |
| DE | 102010046459 | 3/2012 |
| EP | 0880948 | 12/1998 |
| EP | 1870057 A1 | 12/2007 |
| EP | 2085050 A1 | 5/2009 |
| EP | 2329796 | 6/2011 |
| EP | 2489331 | 8/2012 |
| JP | 2002525162 | 8/2002 |
| JP | 2007507301 | 3/2007 |
| JP | 2010522015 | 7/2010 |
| WO | 0018322 | 4/2000 |
| WO | 2005089674 | 1/2005 |
| WO | 2005089672 | 9/2005 |
| WO | 2006047520 A2 | 5/2006 |
| WO | 2006069094 A1 | 6/2006 |
| WO | 2009017827 | 2/2009 |
| WO | 2009085206 | 7/2009 |
| WO | 2009094188 | 7/2009 |
| WO | 2009153768 | 12/2009 |
| WO | 2010024868 | 3/2010 |
| WO | 2010098857 | 9/2010 |
| WO | 2010124286 | 10/2010 |
| WO | 2011104269 | 9/2011 |
| WO | 2012035550 | 3/2012 |
| WO | 2012103501 A1 | 8/2012 |

OTHER PUBLICATIONS

International Search Report and Written Opinion dated Mar. 29, 2013 for PCT/US2012/060364.

International Search Report and Written Opinion dated May 15, 2014 for PCT/US2012/060364.

International Search Report and Written Opinion dated Jun. 10, 2014 for PCT/US2014/020187.

International Search Report and Written Opinion dated Jul. 1, 2014 for PCT/US2014/022328.

International Search Report and Written Opinion dated Aug. 16, 2012 for PCT/US2012/35851.

International Search Report and Written Opinion dated Sep. 13, 2013 for PCT/US2013/044013.

International Search Report and Written Opinion datedOct. 16, 2012 for PCT/US2012/060364.

Material Safety Data Sheet, © 2010 Polymer Systems Technology Limited™ UK & Ireland Distributor, NUSIL Silicone Technology. Effective Feb. 8, 2010. pp. 1-9.

Notice of Allowance dated Dec. 23, 2014 for U.S. Appl. No. 12/285,358.

Office Action dated Jan. 6, 2014 for U.S. Appl. No. 13/285,356.

Office Action dated Jan. 13, 2015 for U.S. Appl. No. 13/153,150.

Office Action dated Jan. 29, 2015 for U.S. Appl. No. 13/352,926.

Office Action dated Mar. 13, 2015 for U.S. Appl. No. 14/196,012.

Office Action dated Apr. 9, 2015 for U.S. Appl. No. 14/202,128.

(56) References Cited

OTHER PUBLICATIONS

Office Action dated Apr. 18, 2013 for U.S. Appl. No. 13/153,150.
Office Action dated May 15, 2013 for U.S. Appl. No. 13/285,356.
Office Action dated Jun. 19, 2014 for U.S. Appl. No. 13/153,150.
Office Action dated Jun. 30, 2015 for U.S. Appl. No. 13/909,427.
Office Action dated Sep. 10, 2015 for U.S. Appl. No. 13/153,150.
Office Action dated Sep. 28, 2015 for U.S. Appl. No. 14/196,012.
Office Action dated Oct. 17, 2014 for U.S. Appl. No. 13/909,427.
Office Action dated Nov. 6, 2012 for U.S. Appl. No. 13/153,150.
Office Action dated Jun. 19, 2014 for U.S. Appl. No. 13/352,926.
Notice of Allowance dated Aug. 26, 2016 for U.S. Appl. No. 14/196,012.
Extended European Search Report dated Jul. 22, 2016 for EP14759720.7.
Office Action dated Mar. 29, 2016 for U.S. Appl. No. 14/202,128.
Office Action dated Apr. 27, 2016 for U.S. Appl. No. 13/153,150.
Office Action dated May 11, 2016 for U.S. Appl. No. 13/909,427.
European Search Report dated Jan. 27, 2016 for EP13801042.6.
Office Action dated Feb. 17, 2016 for U.S. Appl. No. 14/196,012.
Notice of Allowance dated May 5, 2017 for U.S. Appl. No. 13/909,427.
Office Action dated Feb. 8, 2017 for U.S. Appl. No. 13/153,150.
Office Action dated Feb. 28, 2017 for U.S. Appl. No. 14/202,128.
Office Action dated Nov. 8, 2016 for U.S. Appl. No. 14/202,128.
Office Action dated Dec. 19, 2016 for U.S. Appl. No. 13/909,427.
Extended European Search Report dated Sep. 9, 2016 for EP14767746.2.

* cited by examiner

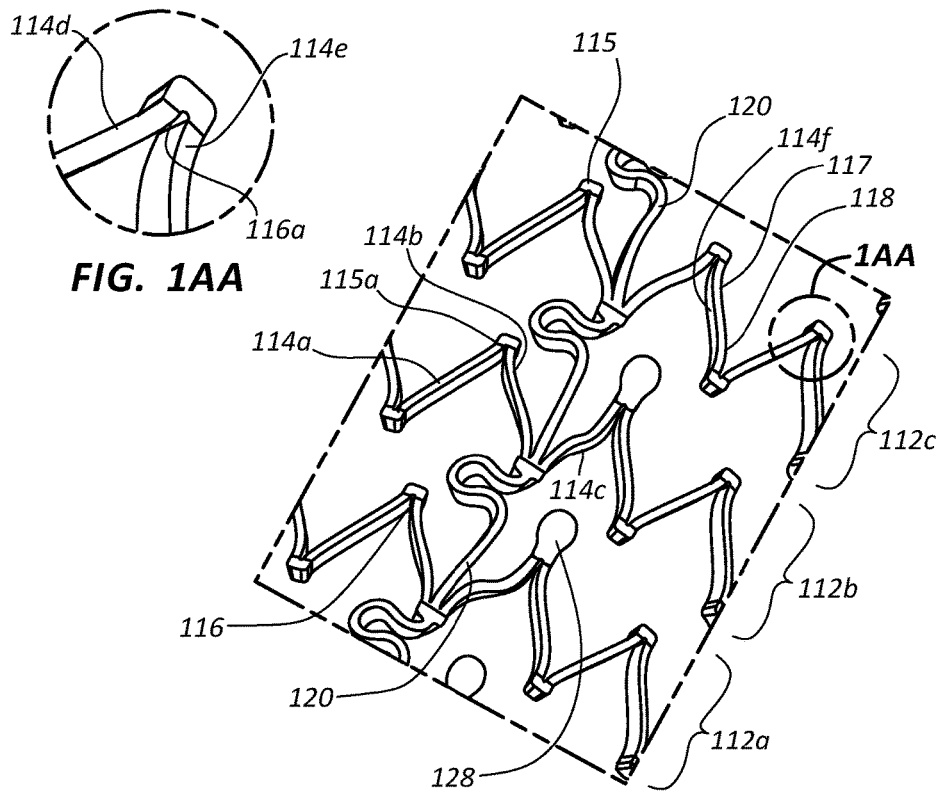
FIG. 1AA
FIG. 1A
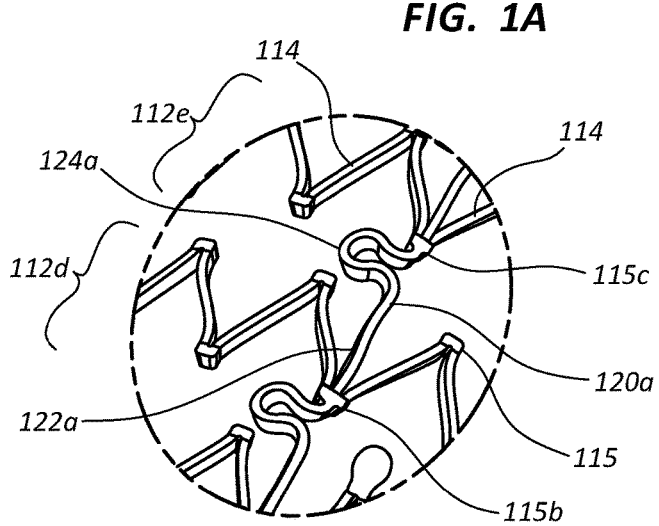
FIG. 1B

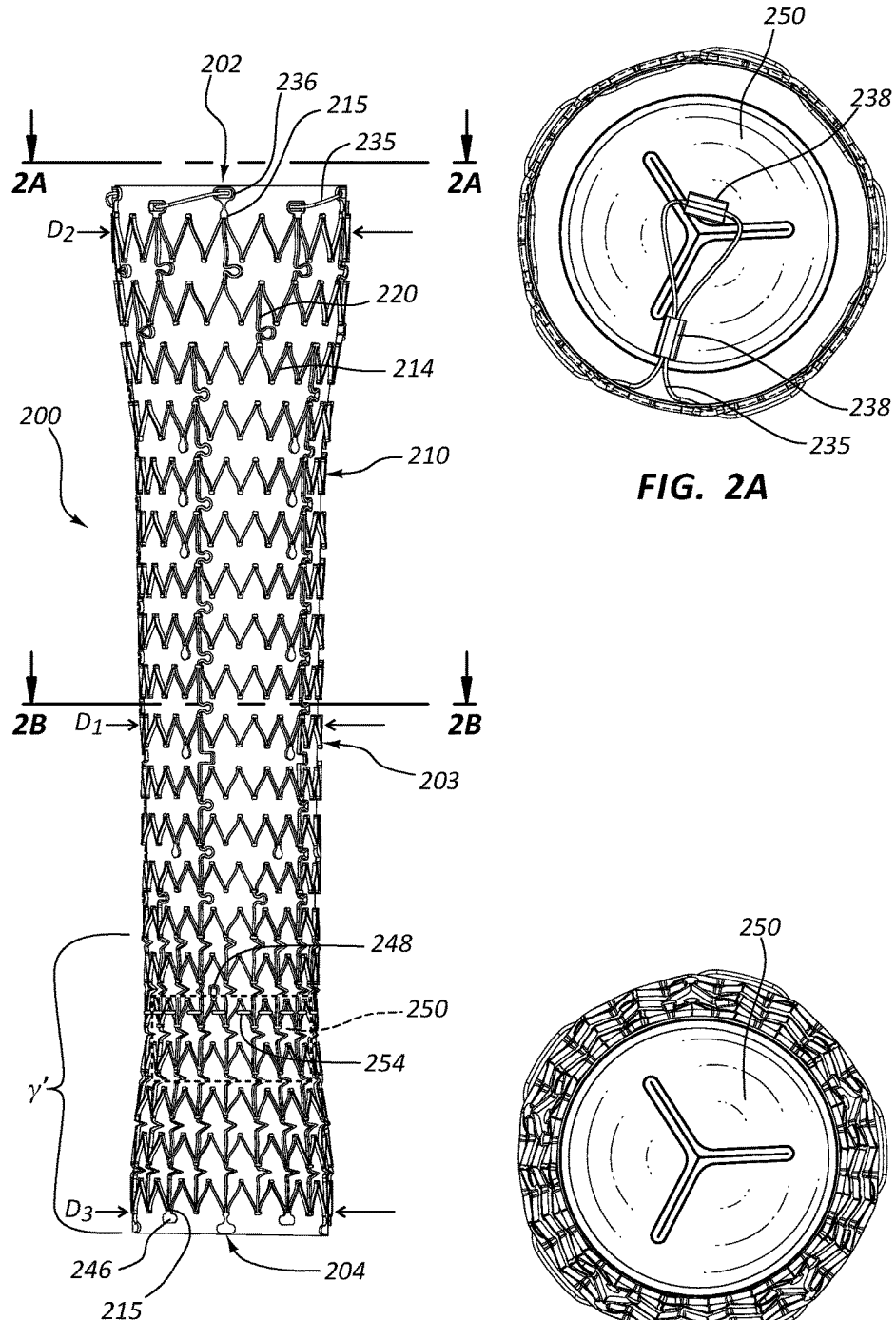

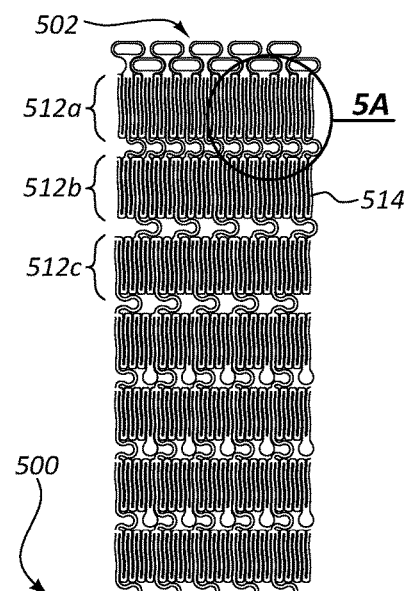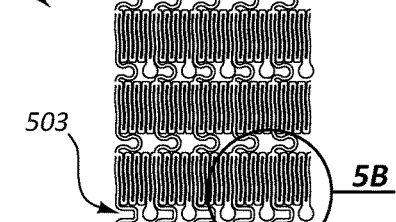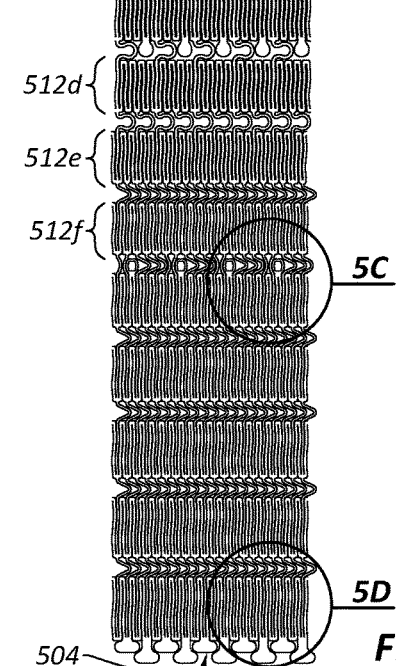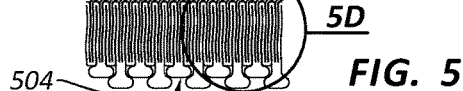
FIG. 5
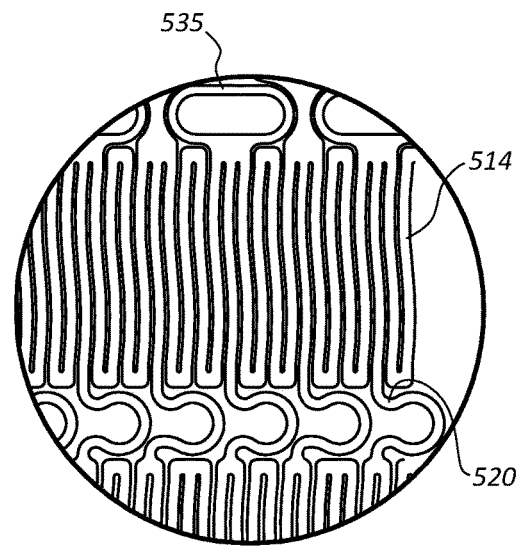
FIG. 5A
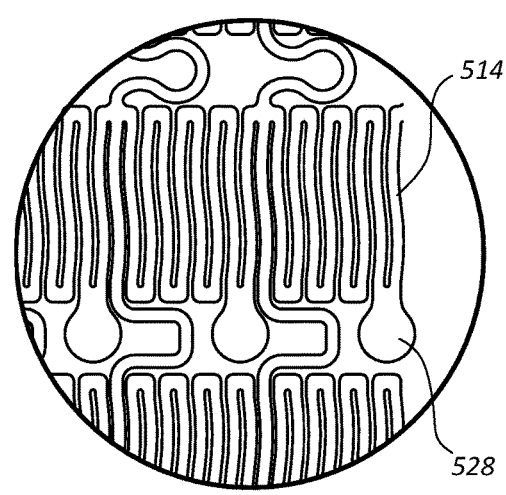
FIG. 5B

ESOPHAGEAL STENT WITH VALVE

RELATED APPLICATIONS

The present application is a continuation of copending U.S. application Ser. No. 13/285,358, filed on Oct. 31, 2011 and titled, "Esophageal Stent With Valve," which is hereby incorporated by reference in its entirety.

TECHNICAL FIELD

The present disclosure relates generally to devices configured to be implanted within a body lumen. More particularly, the present disclosure relates to stents or similar prosthetic devices which, in certain embodiments, are configured to be disposed within the esophagus and which may comprise a valve.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a close up view of a portion of the stent of FIG. 1.
FIG. 1AA is a further close up view of a portion of FIG. 1.
FIG. 1B is a second close up view of a portion of the stent of FIG. 1.
FIG. 2 is a front view of another embodiment of a stent.
FIG. 2A is a top view of the stent of FIG. 2, taken through line 2A-2A.
FIG. 2B is a cross-sectional view of the stent of FIG. 2, taken through line 2B-2B.
FIG. 5 is a side view of a stent in an unexpanded state. More particularly,
FIG. 5 is a side view of an unexpanded stent in a "rolled out" state, depicted as if the stent were cut in the longitudinal direction and rolled out flat such that the entire circumference of the stent may be viewed flat.
FIG. 5A is a close up view of the stent of FIG. 5.
FIG. 5B is a second close up view of the stent of FIG. 5.

DETAILED DESCRIPTION

A stent may be configured with a support or scaffolding structure that may optionally be coupled to a covering. Additionally, the stent may comprise a variety of components, and the parameters of these components—such as shape, length, thickness, position, etc.—may be configured to provide a stent with certain properties. For example, the stent may be configured to distribute transverse loads or to change shape in response to certain forces. In some embodiments, the stent may also include a suture which may aid the user with repositioning or removal of the stent. Furthermore, the stent may comprise a valve which may be coupled to the inside diameter of the stent.

Though many of the examples provided herein refer to stents configured for use within the esophagus, the present disclosure is also applicable to a variety of stents designed for a variety of applications—for example, biliary stents.

It will be readily understood with the aid of the present disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner during use, while the distal end is the opposite end. For example, the proximal end of a stent refers to the end nearest the practitioner when the stent is disposed within, or being deployed from, a deployment device. For consistency throughout, these terms remain constant in the case of a deployed stent, regardless of the orientation of the stent within the body. In the case of an esophageal stent—deployed through the mouth of a patient—the proximal end will be nearer the head of the patient and the distal end nearer the stomach when the stent is in a deployed position.

Figure 1:
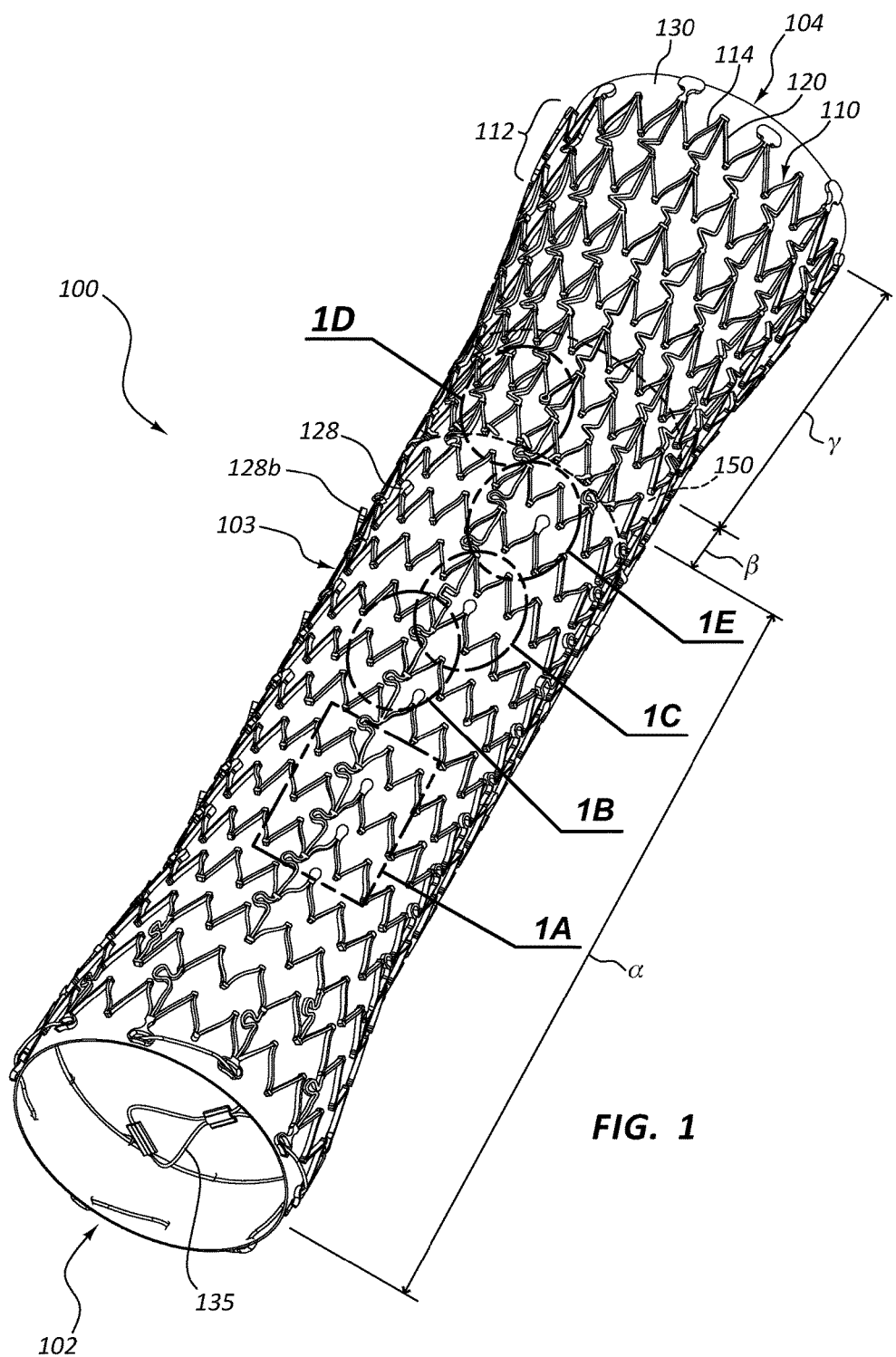
FIG. 1 is a perspective view of a stent.

FIG. 1 is a perspective view of one embodiment of a stent 100. In the illustrated embodiment, the stent 100 has a substantially cylindrical shape and defines a proximal end 102 and a distal end 104. The stent 100 may include a scaffolding structure 110 formed of multiple interconnected segments, a covering 130 coupled to the scaffolding structure 110, a suture 135, and a valve 150.

The scaffolding structure 110 may be comprised of any material known in the art, including memory alloys. In some embodiments the scaffolding structure 110 may be constructed of nitinol, including ASTM F2063. The thickness of the scaffolding structure 110 may be from about 0.30 mm to about 0.6 mm, or greater; in some embodiments including thicknesses from about 0.35 mm to about 0.55 mm, thicknesses from about 0.40 mm to about 0.50 mm, and thicknesses of about 0.47 mm.

The scaffolding structure 110 may be formed of multiple annular segments or rings 112 arranged in rows along the longitudinal direction of the stent 100. Each annular segment 112 may be comprised of interconnected strut arms 114. In the illustrated embodiment, the strut arms 114 are connected such that they form a zigzag pattern, the pattern defining alternating "peaks" and "valleys," around the annular segment 112. In some embodiments adjacent strut arms 114 will form acute angles relative to each other. Adjacent annular segments 112 may be coupled to each other by connectors 120.

The stent 100 may further be configured with a valve 150. In some embodiments, such as the embodiment of FIG. 1, the valve 150 may be coupled to the inside diameter of the stent 100. Thus, the valve 150 is not directly visible in the illustration of FIG. 1, though its position is indicated by a reference line.

In some embodiments the stent 100 may be divided into one or more zones along the longitudinal length of the stent 100. For example, a stent 100 may be configured such that different segments or zones of the stent have different structural or geometric features or components. For example, the stent 100 shown in FIG. 1 may be separated into three longitudinal zones or segments: a proximal zone, α; a transition zone, β; and a valve zone γ. In some embodiments a stent 100 may be designed such that the proximal zone α is relatively "softer" (meaning more compressible in a transverse direction) than the valve zone γ. In some applications, the relative softness of the proximal zone may be configured to cause less trauma to tissue which contacts an implanted stent 100. Further, the softness of the proximal end may be configured to aid in the removal or repositioning of the stent 100. Analogously, a "harder" valve zone γ may provide additional structure and support to prevent deformation or collapse of the valve 150. Furthermore, in some instances, the valve zone γ may be configured to be positioned at a particular physiologic position, such as the lower esophageal sphincter in the case of an esophageal stent. The hardness of the valve zone may be configured to resist deformation by strictures of other physiologic features or conditions at the therapy site. Finally, the transition zone β may be configured as an intermediate zone, with properties configured to fall between those of the proximal zone α and the valve zone γ.

FIG. 1A is a close up view of a portion of the proximal zone α of the stent 100 of FIG. 1. FIG. 1A includes portions of three adjacent annular segments, designated 112a, 112b, and 112c. Throughout this disclosure, particular examples of components may be designated by a letter following the reference numeral. For example, reference numeral 112 refers generally to the annular segments of the stent 100. Specific annular segments, such as those shown in FIG. 1A, are thus labeled 112a, 112b, and 112c. This pattern of identifying particular examples of general or repeating components may be used throughout this disclosure.

In the illustrated embodiment, each annular segment 112a, 112b, 112c includes multiple strut arms 114, which are arranged in zigzag patterns. For example, strut arm 114a is coupled to strut arm 114b, such that the two arms 114a, 114b form a peak in the zigzag pattern. Strut arm 114b is further coupled to strut arm 114c such that the two arms 114b, 114c form a valley in the zigzag pattern.

In the illustrated embodiment, adjacent strut arms, such as arms 114a, 114b, are coupled at an apex, such as apex 115a. The angle formed at the apexes 115 by two adjacent strut arms 114 may be designed to provide the stent 100 with particular properties. For example, in the illustrated embodiment the angle formed at each apex 115 is about 45 degrees. In other embodiments this angle may be from about 30 degrees to about 60 degrees including angles from about 40 degrees to 50 degrees. As discussed in more detail below, apex 115 angles of about 45 degrees, as well as angles within the aforementioned ranges, may aid with balancing forces in the X and Y directions on the stent 100 to prevent infolding of the stent.

As used herein, infolding refers to inward protrusions or wrinkles that may form along the inside diameter of a stent in response to unbalanced transverse compressive forces on the stent. For example, an esophageal stent may infold as a result of the peristaltic motion of the esophagus. In other instances, a stent may infold due to forces exerted by an uneven portion of the body lumen, such as a stricture or buildup of scar tissue.

Furthermore, a cylindrical stent may define a set of transverse planes located perpendicular to the longitudinal axis of the stent. As used herein, transverse forces are forces acting in any of these planes. Further, as used herein, the X and Y directions refer to a coordinate system in any of these planes. A stent designed to generally balance compressive forces in the X and Y directions may tend to resist infolding. In other words, a stent may have compressive forces applied unevenly in different transverse directions. The design of the stent may be configured to transfer these forces such that the stent distributes the load more evenly around the circumference of the stent. In particular, the approximately 45 degree angles between adjacent arm struts 114 in stent 100 may transfer uneven loads further allowing the stent 100 to resist infolding. Likewise, other angles disclosed herein may also distribute transverse forces.

In some embodiments, the inner surface of the apex 115 may be substantially circular or semi-circular in shape, forming an inner radius 116. The inner radius 116 of the apex 115 may be sized so as to impart particular characteristics to the stent 100. For example, as illustrated in FIG. 1AA, the radius 116a may be large as compared to the angle formed by the two inner surfaces of the coupled strut arms 114d, 114e. In such instances, the inner surfaces of the strut arms 114 and the radius 116 may form a rough "keyhole" shape. In other embodiments, the radius 116 and strut arms 114 may not form a keyhole shape, though the radius 116 is still relatively large. Designs that incorporate relatively large radii 116 may provide desired characteristics to the stent 100, such as surface finish, fatigue life, and fracture resistance. The size of the radius 116 may vary depending on the desired properties of the stent 100. In some embodiments the radius 116 may be from about 15 microns to about 95 microns including embodiments where the radius is from about 30 microns to about 80 microns or from about 45 microns to about 65 microns.

Moreover, in certain embodiments, the stent 100 may be designed with different radii 116 in different portions of the stent 100. In some embodiments, for example, the geometric features of certain zones may impact the size of the radii 116 within that zone. In portions of the stent 100 with relatively more connectors 120, less material may be available to allow for large radii 116. In one embodiment a stent 100 may be designed such that the radii are from about 40 microns to about 60 microns, including radii of about 54 microns, in portions of the stent 100 with about five connectors 120 around the circumference of the stent (such as most of the proximal zone, α of the illustrated stent 100). Similarly, portions of the stent 100 with about 10 connectors 120 around the circumference of the stent 100 may have radii 116 from about 25 microns to about 45 microns, including radii of about 35 microns. Finally, portions of the stent 100 with about 20 connectors around the circumference of the stent 100 may have smaller radii 116, such as from about 10 microns to about 20 microns, including radii of about 15 microns. It will be appreciated by one of skill in the art having the benefit of this disclosure that these values may vary in differing designs; for example, a stent 100 may be cut with a relatively large number of connectors 120, but with relatively narrow connectors 120 to allow more material for larger radii 116.

Each strut arm 114 may define a length along the strut arm 114. Again, as shown in both FIG. 1 and FIG. 1A, each strut arm 114 is coupled to two other strut arms 114, forming apexes 115 on both ends of the strut arm 114. The length of a single strut arm 114 is the length of the strut arm 114 from a first end to a second end, or the distance between each apex 115 at which the strut arm 114 is coupled to an adjacent strut arm 114.

The relative lengths of the strut arms 114 may affect the overall properties of the stent 100. For instance, portions of the stent 100 that have relatively longer strut arms 114 may be "softer" (again, meaning more compressible in a transverse direction) than portions of the stent 100 where the strut arms 114 are relatively shorter. In the embodiment illustrated in FIG. 1, the stent arms 114 located adjacent the proximal 102 and distal 104 ends are relatively longer than those along subsequent annular segments 112, moving toward the mid-body 103 of the stent 100. Thus, the stent 100 illustrated in FIG. 1 may be stiffer, or less compressible in a transverse direction, at the inner portions of the proximal α and valve γ zones, as compared to the portions of these zones adjacent the proximal 102 and distal 104 ends of the stent 100.

In other embodiments, the stent 100 may also be configured such that the strut arms 114 located near the proximal 102 end are relatively longer than the strut arms 114 located near the distal 104 end. Accordingly, the stent 100 may also be softer near the proximal end 102 relative to the distal end 104. In other embodiments, a stent may be designed with strut arms of uniform length throughout, of a particular length along certain portions of the stent (for example, near both the proximal and distal ends), or of varying lengths along the entire stent. Further, in some embodiments, strut arm 114 length will be substantially constant for all strut arms 114 located on the same annular portion 112; in other embodiments strut arm 114 length may vary within a single annular portion 112.

In some embodiments, a stent may be configured with softer zones in order to tailor the stent to a specific therapy. For example, a stent designed with relatively soft ends may result in relatively less discomfort, or pain, caused by contact of the stent ends with body tissue. Thus, in some embodiments the portion of the stent 100 configured to be implanted at the treatment location may be relatively stiff—allowing it to resist stricture and otherwise function as part of the treatment—while other portions are relatively soft to reduce trauma and pain at those points.

In certain embodiments, the strut arms 114 may be curved. Strut arm 114*f* illustrated in FIG. 1A, for example, may be understood as having a first portion 117 and a second portion 118. The first 117 and second 118 portions may or may not be the same length. Strut arm 114*f* is generally formed with an inflection point located between the first 117 and second 118 portions of the strut arm 114*f*. Thus, in the illustrated embodiment, the strut arm 114*f* may be curved in the general shape of a sigmoid curve. In other words, the first portion 117 of the strut arm 114*f* forms a first roughly arcuate path, and the second portion 118 of the strut arm 114*f* forms a second roughly arcuate path. In the illustrated embodiment, the center of the first arcuate path is on the opposite side of the arm than the center of the second arcuate path. Thus, the strut arm 114*f* has a wave-like shape formed by the strut arm 114*f* starting to curve in one direction, then curving in a second direction. Accordingly, strut arm 114*f* has an "inflection point" at or around the point where the first portion 117 meets the second portion 118. In the embodiment of FIG. 1, each strut arm 114 is shaped substantially as described in connection with strut arm 114*f*.

In other embodiments, the strut arms 114 may have a single curve, may be substantially straight, or may resemble other types of curves. Furthermore, while in some instances each strut arm 114 may have a curved shape similar to the other strut arms 114 of the stent 100, in other embodiments multiple strut arms 114 on the same stent—including strut arms 114 disposed in the same annular segment 112—may have different shapes.

As shown in FIGS. 1 and 1A, adjacent annular segments 112 may be coupled by connectors 120. In some embodiments, the connectors 120 may be coupled to the annular segments 112 at the apexes 115 formed by adjacent strut arms 114. In the embodiment of FIGS. 1 and 1A, the connectors 120 of adjacent annular segments 112 are aligned in the circumferential direction along the longitudinal direction of the stent 100 for all rows except the three rows of annular segments 112 nearest the proximal end 102 of the stent 100. In other embodiments, the connectors 120 may be offset circumferentially along the longitudinal direction of the stent 100, or aligned, along any longitudinal segment of the stent 100.

Furthermore, in certain embodiments, such as the embodiment of FIG. 1, a stent 100 may be configured with different numbers of connectors 120 per annular segment 112, along the length of the stent 100. In the embodiment of FIG. 1, the stent 100 has more connectors 120 per annular segment 112 in the valve zone γ than in the transition zone β, and more connectors 120 per annular segment 112 in the transition zone β and the valve zone γ than in all but the first row of the proximal zone α. Specifically, the illustrated embodiment has about twenty connectors 120 per annular segment 112 in the valve zone γ, about ten connectors 120 per annular segment 112 in the transition zone β and about five connectors 120 per annular segment 112 in all but the proximal-most row of the proximal zone α. In other embodiments the absolute number of connectors in each zone may vary from these values, as may the ratio of connectors 120 per annular segment 112 in each zone.

The number of connectors 120 included in a particular zone may be configured to affect the properties of the stent 100 in that zone. For example, the proximal-most row of the stent 100 may be configured with 10 or more connectors 120 to provide more uniform crimping as compared to sections of the stent 100 with only five connectors 120 per annular segment 112. In different embodiments, the number of connectors 120 associated with any annular segment 112 may vary from about four connectors 120 per annular segment 112 to about 20 connectors 120 per annular segment 112.

In the illustrated embodiment, the stent has about ten connectors connecting the proximal-most annular segment 112 to the adjacent segment. In other embodiments the stent 100 may be configured with the same number (five, ten, or some other number) of connectors per annular segment 112 throughout the entire proximal zone α.

In embodiments wherein the stent has more connectors at the proximal-most end than the rest of the proximal zone (such as the embodiment of FIG. 1), the greater number of connectors may be configured for a number of functions. For example, a greater number of connectors at the proximal end may be configured to add resiliency and strength to the end of the stent. In particular, in embodiments where the ends of the stent flare out to relatively large diameters, additional connectors may add strength to minimize the potential for infolding at the oversized end. Additionally, a larger number of connectors may be configured to provide for more uniform crimping of the stent in preparation for loading the stent into a catheter, and for more uniform expansion upon deployment. Though the embodiment of FIG. 1 only has additional connectors associated with the proximal-most annular segment, in other embodiments a stent may have additional connectors associated with more than one row near the proximal end. For example, the first 1, 2, 3, 4, 5, or more proximal-most annular segments may be configured with additional connectors.

Further, in the illustrated embodiment, the connectors 120 linking the first three rows of annular segments 112, beginning with the proximal-most row 112, are offset circumferentially from each other. This alternating alignment of the connectors, as well as the thickness of the scaffolding structure, may be configured to enable a stent, such as stent 100, to resist infolding. For example, in some instances the alternating alignment of the connectors may tend to localize stent deformation caused by strictures in the lumen, rather than transferring such deformations along the length of the stent. In some embodiments the connectors may be offset at one or both ends of the stent 100 due to increased concern for infolding at the ends of the stent 100. This may be particularly true in stents 100 with flared ends, which have a more open (and therefore softer) scaffolding structure near the ends. The illustrated embodiment has alternating connectors associated with the three proximal-most annular segments; other embodiments may have more or fewer rows with alternating segments, including 1, 2, 3, 4, 5, or 6 annular segments.

As with varying the lengths of strut arms 114, described above, variations in the number of connectors 120 per annular segment 112 may affect the relative hardness of the stent 100. Generally, portions of the stent 100 with a larger number of strut arms 114 per annular segment 112 may be relatively harder than portions with fewer connectors 120. Thus, the stent 100 illustrated in FIG. 1 may be relatively harder in the transition zone β and the valve zone γ than in the proximal zone α. In some embodiments this may provide additional support and strength to support the valve 150. The relative hardness of different portions of each zone may not be constant, however, due to other factors such as strut arm 114 length, discussed above.

FIG. 1B is a close up view of a portion of the proximal zone α of the stent 100 of FIG. 1, showing a particular connector 120a. The connector 120a couples two adjacent annular portions 112d, 112e together, and is coupled to each annular portion 112d, 112e at apexes 115b, 115c on each annular portion. Connector 120a has a first portion 122a and a second portion 124a. In the illustrated embodiment, the first portion 122a is relatively straight and spans much of the distance between the adjacent annular segments 112. In other embodiments, the first portion 122a may be more or less curved than the first portion 122a of the illustrated embodiment. The second portion 124a may be substantially formed in a rounded shape, in some instances forming the general profile of the symbol omega (Ω). In some embodiments, the omega-shaped second portion 124a may add axial strength to the stent 100. In some instances, axial strength may be desirable for repositioning or removing a stent 100.

Further, in some embodiments, omega-shaped connectors may add flexibility and/or elasticity to the stent 100. The omega shape, having two ends relatively near each other connected by a relatively long curved member (the round portion of the omega) may be configured to provide added flexibility to the stent.

The other connectors 120 within the proximal zone α of the embodiment of FIG. 1 are generally shaped like connector 120a disclosed above, with the exception of one row of connectors located at about the mid-body of the stent 100, as discussed in more detail below. It is within the scope of this disclosure, however, to use any type or shape of connector at any point along the stent.

At the portion of the stent 100 shown in FIG. 1B, the adjacent annular segments 112d, 112e are aligned such that apexes 115 at the peak of the zigzag pattern in annular segment 112d are circumferentially aligned with apexes 115 at the peak of the zigzag pattern of the adjacent annular segment 112e. The connector 120a couples the two adjacent annular segments 112d, 112e by coupling to valley apex 115b of annular segment 112d and to valley apex 115c of annular segment 112e. (As used herein, "peaks" refer to high points and "valleys" refer to low points, as measured from one end of the stent. Thus the coupling of the two segments just described may also be described as a "peak to peak" connection, if viewed from the opposite orientation.) In some embodiments, a stent may be designed such that the peaks and valleys of adjacent annular segments are circumferentially aligned, such as annular segments 112d and 112e. In other embodiments, the peaks and valleys of adjacent annular segments may be circumferentially offset.

Figure 1C:
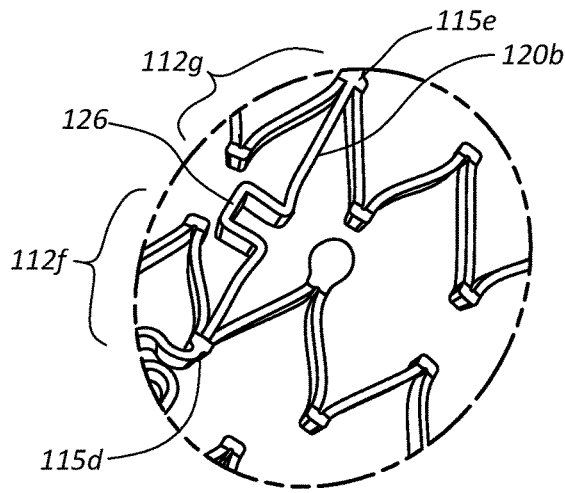
FIG. 1C is a third close up view of a portion of the stent of FIG. 1.

In the embodiment of FIG. 1, the peaks of each annular segment 112 are approximately circumferentially aligned with the peaks of adjacent annular segments 112, at all points along the stent 100 except one set of adjacent annular segments located at the mid-body 103 of the stent 100. FIG. 1C is a detailed view of two adjacent annular segments 112f, 112g located near the mid-body 103 of the stent 100. (Note: Annular segment 112f of FIG. 1C is the same annular segment as annular segment 112e of FIG. 1B.)

Annular segments 112f, 112g are oriented such that the peaks of annular segment 112f are circumferentially aligned with the valleys of annular segment 112g, and the valleys of annular segment 112f are circumferentially aligned with the peaks of annular segment 112g. It will be appreciated by one of skill in the art having the benefit of this disclosure, that in alternative embodiments any combination of alignment/non-alignment of peaks and valleys between any set of annular segments is within the scope of this disclosure.

Annular segments 112f and 112g are coupled to a connector 120b at apex 115d and apex 115e, respectively. Connector 120b extends between each apex 115d, 115e and includes a generally U-shaped or square portion 126 located near the center of the connector 120b. Connectors such as connector 120b, which span between a peak and a valley, may be configured to impart more flexibility to the stent 100 than relatively shorter peak to valley connectors. As with the omega-shaped connectors disclosed above, it is within the scope of this disclosure to use a connector with a square portion, such as connector 120a of FIG. 1B, at any point along the stent.

Figure 1D:
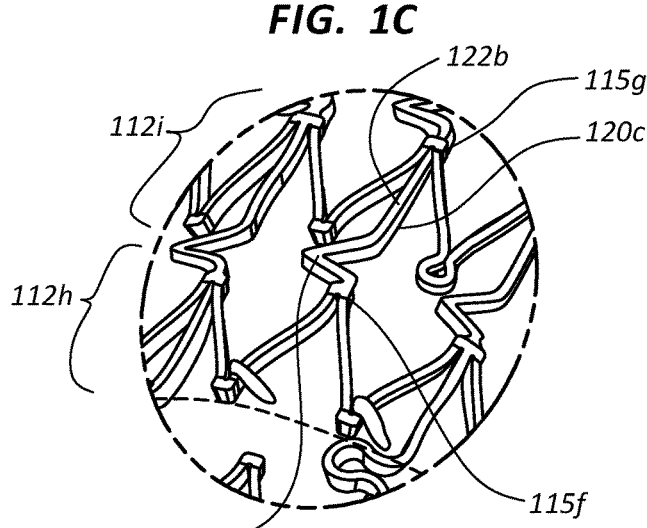
FIG. 1D is a fourth close up view of a portion of the stent of FIG. 1.

FIG. 1D is a close up view of a portion of the valve zone γ of the stent 100 of FIG. 1, showing a particular connector 120c. Similar to connector 120a of FIG. 1B, The connector 120c couples two adjacent annular portions 112h, 112i together, and is coupled to each annular portion 112h, 112i at apexes 115f, 115g on each annular portion. Again, similar to connector 120a of FIG. 1B, connector 120c has a first portion 122b and a second portion 124b. In the illustrated embodiment, the first portion 122b is relatively straight and spans much of the distance between the adjacent annular segments 112. In other embodiments, the first portion 122b may be more or less curved than the first portion 122b of the illustrated embodiment. The second portion 124b may be substantially formed in a V-shape.

In some embodiments, such as the embodiment of FIG. 1, V-shaped connectors may be used in place of, or in connection with, omega-shaped connectors as described above. V-shaped connectors may be used in place of omega-shaped connectors in applications where the additional axial strength provided by omega-shaped connectors is not necessary; for example, in the embodiment of FIG. 1 the axial strength provided by 20 total connectors per annular segment may obviate the need for omega-shaped connectors for some applications. Further, V-shaped connectors may reduce the force required to crimp a stent for loading into a catheter. Additionally, the shape of the connectors 120 may be influenced by the surrounding geometry of the stent 100. For example, the gap between adjacent annular segments 112 and the total number of connectors 120 per annular segment 112 may limit the amount of material available to be shaped into a connector 120. In some embodiments, for example, omega-shaped connectors 120 (which require relatively more material) may not be feasible in zones with a large number, such as 20, of connectors 120 per annular segment 112. V-shaped connectors 120 (which require relatively less material) may be more feasible in such zones.

In the embodiment of FIG. 1, omega-shaped connectors are utilized in the transition zone β of the stent 100. It is within the scope of this disclosure to use any shape of connector within any zone, or to use multiple shapes within the same zone.

Figure 1E:
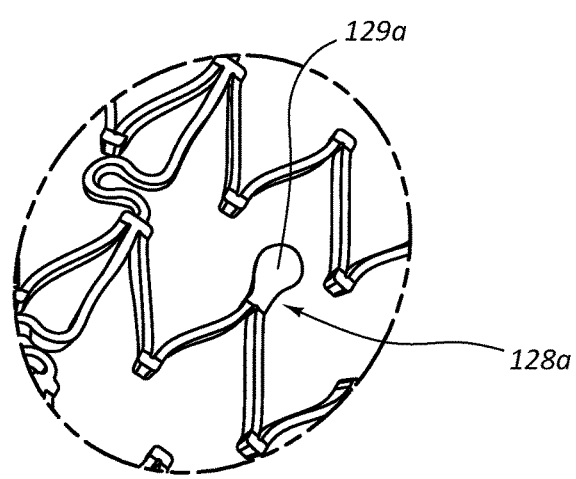
FIG. 1E is a fifth close up view of a portion of the stent of FIG. 1.

The stent 100 of FIG. 1 further includes generally rounded anti-migration portions 128 coupled to certain apexes 115 within the proximal zone α. FIGS. 1A and 1E show close up views of anti-migration portions 128, including anti-migration portion 128a of FIG. 1E. In some embodiments, the anti-migration portion 128a may be configured to contact portions of the inside diameter of a body lumen, and thus restrict migration of the stent 100 within the body lumen. The rounded head 129a of the anti-migration portion 128a, may be from about 0.75 mm in diameter to about 1.5 mm in diameter, including embodiments from about 1.0 mm to about 1.3 mm or embodiments with a diameter of about 1.2 mm.

In certain embodiments, the anti-migration portions 128 may be positioned such that the rounded head 129 is displaced outward of the outside diameter of the stent 100. For example, anti-migration portion 128b of FIG. 1 is disposed outward from the outside diameter of the stent 100. This arrangement may allow anti-migration portion 128b to engage the body lumen and minimize migration of the stent 100. In the embodiment of FIG. 1, each anti-migration portion 128 is disposed outwardly as anti-migration portion 128b, though in other embodiments not every anti-migration portion may be so disposed.

The total number of anti-migration portions may vary depending on the size of the stent and the application for which it is configured. For example, an esophageal stent having a length of about 100 mm may include from about 15 to about 25 anti-migration portions, including about 20 total anti-migration portions. Similarly an esophageal stent having a length of about 120 mm may include from about 25 to 35 anti-migration portions, including about 30 total anti-migration portions, and an esophageal stent having a length of about 150 mm may include from about 35 to 45 anti-migration portions, including about 40 anti-migration portions.

In the embodiment of FIG. 1, each anti-migration portion 128 is disposed in a distally oriented direction, thus configured to minimize migration of the stent 100 in the distal direction. In the case of an esophageal stent, such a design may be configured to counteract the peristaltic forces of the esophagus. In other embodiments, some or all of the anti-migration portions 128 may likewise be disposed in the proximally oriented direction.

The stent 100 of FIG. 1 further includes a covering 130 coupled to the scaffolding structure 110, the covering 130 defining an inner portion of the stent 100. The covering 130 may be elastomeric, polymeric, or comprised of any other material known in the art. In some embodiments, the cover may include silicone, while in certain embodiments the cover may be comprised only of silicone.

In some embodiments, the cover 130 may be applied such that it tends to ebb and flow into spaces between portions of the scaffolding structure 110 of a stent, resulting in a "tire tread" like outer surface, rather than a smooth outer covering. In some embodiments such a design may be configured to allow tissue to lock into the uneven spaces and treads, thus adding anti-migration properties in some instances.

In some embodiments the cover 130 may include multiple subparts or layers. For example, in some embodiments the cover 130 may be a two-part design. Such two-part covers may be composed of a base cover which encapsulates the scaffolding structure 110 and a second cover which may be applied after the first cover cures. In certain embodiments the second cover may only be applied to the outside diameter of the stent 100 and may chemically bond to the first cover layer. For example, a stent may have a covering with a first layer comprised of a medical grade silicone such as TSP-8021, and a second cover, applied to the outside diameter of a particularly low friction silicone, such as Nusil MED-6670. Multiple layered coverings may be configured such that the primary layer adds elasticity or resiliency to the stent while the second, outer layer reduces friction along the outside diameter. It is within the scope of this disclosure to use any of the exemplary materials for any of the layers.

In embodiments which utilize a particularly low friction cover on the outside diameter of the stent 100, the outer cover may be configured to more easily allow the stent to be loaded into a catheter and/or to decrease the catheter size necessary to sheath the stent 100. Specifically, a low friction outer layer, such as Nusil MED-6670 disclosed above, may reduce the coefficient of friction between a catheter and a stent by as much as 50% in some applications.

Further, an additional lubricant, such as Nusil MED-400, for example, may be utilized to increase the ergonomics of the system, allowing the stent 100 to be more easily loaded into, or deployed from, a catheter. In some embodiments silicone lubricants may be used, including fluorinated polymers such as MED-400. Use of fluorination may reduce the solubility of the lubricant in some silicone elastomers; thus use a fluorinated lubricant may reduce the tendency of the lubrication to dissolve into the silicone base over time.

Additionally, the stent 100 of FIG. 1 includes a suture 135 disposed adjacent the proximal end 102 of the stent 100. The suture 135 may be configured as a repositioning or removal aid, allowing a practitioner to capture a deployed stent. In other embodiments the stent 100 may also or alternatively comprise a suture (not shown) disposed adjacent the distal end 104 of the stent 100.

The features and elements of the stent 100 of FIG. 1 may be configured to create a stent with particular characteristics and features. In addition to the disclosure recited above, the disclosure provided hereinafter—in connection with any figure or discussion—is equally relevant to controlling the characteristics of a finished stent. Any part of the present disclosure may be combined with any other part of the disclosure to configure a stent. Thus, while certain aspects or parameters—for example, strut arm length or flared ends— may be discussed in connection with one embodiment, such disclosure is relevant to all embodiments.

A stent with substantially the geometry and features described in connection with the stent 100 of FIG. 1 may be configured to "neck down" in response to an axial force. In other words, the diameter of the cylindrical stent may be reduced by applying an axial force to the stent. Such necking down may be used in connection with removing or repositioning a deployed stent; the decrease in diameter may pull the stent out of contact with the body lumen, allowing a practitioner to displace the stent while avoiding some trauma to the body lumen.

In some instances this necking down may occur near the ends of the stent, including instances where the stent only necks down at one end of the stent. For example, a practitioner may reposition or remove a stent by first engaging a suture located near one end of the stent. At the suture location the stent may decrease in diameter as force is applied to the suture; in other words the stent may contract or "purse string" as the suture is tightened. In some embodiments the force associated with this purse string effect may be understood as a compressive force acting around the circumference of the stent at the suture location.

Additionally, portions of the stent near the suture may neck down as an axial force is applied to the stent, in some instances the stent necking down to a diameter which is less than the mid-body of the stent. In some embodiments, a stent may be configured such that a force of about 2 pounds causes the stent to neck down as described.

In certain embodiments a stent may be configured to decrease in size, due to one or both of the purse string effect and necking down, primarily at the ends of the stent. In some instances, tissue granulation or other tissue ingrowth into the stent may occur primarily at the ends of the stent. Thus, some stents may be configured to decrease in diameter at the ends to allow a practitioner to dislodge the stent ends from the wall of the body lumen, including in cases where there is tissue granulation at the ends of the stent.

As stated above, each of the elements described above may be manipulated to control the necking down characteristics of a stent. In particular, a stent such as stent 100 of FIG. 1 may neck down due to the elasticity of the covering 130, the thickness of the scaffolding structure 110, and the configuration of the geometry at the ends 102, 104 of the stent 100, including the inclusion of suture eyelets (discussed further below) and the circumferentially alternating arrangement of certain connectors. A stent such as stent 100 may neck down as much as 50% in response to an axial force.

A practitioner may begin the process of repositioning or removing a stent, such as stent 100, by first engaging the sutures. The sutures may be used to compress one end such that the end is pulled away from the lumen wall. The practitioner may then apply an axial force to the end of the stent, causing a portion of the stent to neck down and pull away from the lumen wall. The practitioner may then reposition or remove the stent with minimal trauma to the body lumen.

Additionally, the increased number of connectors in the transition β and valve γ zones may act to decrease infolding in these zones due to the increased strength in the transverse direction associated with more connectors. Likewise, as discussed above, alternating connectors at the proximal end may be configured to aid with infolding.

FIG. 2 is a front view of another embodiment of a stent that can, in certain respects, resemble components of the stent described in connection with FIGS. 1 and 1A-1E above. It will be appreciated that all the illustrated embodiments may have analogous features. Accordingly, like features are designated with like reference numerals, with the leading digits incremented to "2." (For instance, the stent is designated "100" in FIG. 1, and an analogous stent is designated as "200" in FIG. 2.) Relevant disclosure set forth above regarding similarly identified features thus may not be repeated hereafter. Moreover, specific features of the stent and related components shown in FIG. 2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the stent of FIG. 2. Any suitable combination of the features, and variations of the same, described with respect to the stent and components illustrated in FIGS. 1 and 1A-1E, can be employed with the stent and components of FIG. 2, and vice versa. This pattern of disclosure applies equally to further embodiments depicted in subsequent figures and described hereafter.

FIG. 2 is a front view of another embodiment of a stent 200. The stent 200 defines a proximal end 202 and a distal end 204 as well as a mid-body section 203. In some embodiments the stent 200 may have a smaller diameter near the mid-body section 203 than sections of the stent 200 near the proximal 202 and distal ends 204. Thus, in the illustrated embodiment, $D_2$ and $D_3$ may be larger in magnitude than $D_1$. In some embodiments, the mid-body diameter may be constant along a length of the stent 200, with flare portions that gradually increase in diameter near the ends 202, 204. Depending on the desired application, the diameters of the stent 200 may vary. For example, certain stents may be designed with mid-body diameters of about 12 mm to about 25 mm, including stents with diameters from about 19 mm to about 23 mm. In embodiments which include flared zones near the ends of the stent, the diameter of the flared sections may increase from about 2 mm greater to about 8 mm greater than the mid-body diameter of the stent, including increases of about 4 mm to about 6 mm or an increase of about 5 mm or increase of about 2 mm to about 4 mm, including increases of about 3 mm. While in some embodiments the stent 200 may increase by about the same magnitude at both the proximal 202 and distal 204 ends, in other embodiments, such as the embodiment of FIG. 2, the increases may be different. For example, in the embodiment of FIG. 2, $D_2$, or the diameter at the proximal end, may be about 5 mm greater than $D_1$, the mid-body diameter of the stent 200, while $D_3$ may be about 3 mm greater than $D_1$.

In embodiments where the strut arms 214 are relatively longer (creating relatively "softer" zones near the ends 202, 204 of the stent 200) the flare section may correlate with the zones of the stent 200 that have relatively longer strut arms 214. The strut arm 214 length may be configured to gradually increase along the longitudinal direction of the stent 200 in the flare zones.

Similarly, the length of the connectors 220 may gradually increase as the strut arm 214 length increases. Longer connectors 220 and arm struts 214 may generally create a more open scaffolding structure 210 near the ends 202, 204 of the stent 200. In some embodiments, the flare zones may be mirror images of each other; in other embodiments they may be different.

In some embodiments, the flare zones may be formed by stretching or expanding the ends 202, 204 of the stent 200 with respect to the mid-body 203 of the stent 200. This may result in a more open scaffolding structure 210 near the ends of the stent 200. Regions of the stent 200 with a more open scaffolding structure 210 may be relatively softer than regions of the stent 200 which have a denser scaffolding structure 210. Thus, the flared ends of a stent, such as stent 200, may be configured to create a stent with ends which are softer than the mid-body 203 of the stent. As disclosed above, relatively longer strut arms 214 and connectors 220 may also be configured to create softer regions on a stent. Flared ends and changing strut arm 214 and connector 220 lengths may each be designed and/or may utilize independently from, or in connection with, these other parameters in order to create a stent 200 with relatively softer, or stiffer, zones.

The stent 200 may be configured to neck down in a similar manner to that described in connection with the stent 100 of FIG. 1. In some embodiments, the flared portions of the stent 200 may be configured to neck down to a diameter less than the diameter of a mid-body section of the stent. In certain embodiments, a mid-body section may not be configured to neck down.

FIGS. 2A-2B are additional views of the stent 200 of FIG. 2. FIG. 2A is a top view of the stent of FIG. 2, viewing the stent 200 from the proximal end 202, and FIG. 2B is a cross-sectional view of the stent of FIG. 2, taken through line 2B-2B.

As shown in FIG. 2 the stent 200 may include suture threading eyelets 236 or apertures, coupled to one or more apexes 215 of the scaffolding structure 210 at the proximal 202 end of the stent 200. The suture threading eyelets 236 may be configured to receive a suture 235 and couple it to the stent 200.

Furthermore, the suture threading eyelets 236 may comprise holes or apertures which are elongated in the circumferential direction of the stent 200. Such a design may be configured to distribute the expansive force of a stent 200 acting on a body lumen when the stent 200 is deployed. This distribution of force, in connection with the smooth and rounded shape of the eyelets 236, may be configured to lessen the trauma to body tissue which contacts the end 202 of the stent 200.

The suture threading eyelets 236 may be configured to locate the suture 235 substantially at the proximal 202 end of the stent 200. In other words, the eyelets 236 may be positioned such that the entire scaffolding structure 210 is located distal of the eyelets 236. Such positioning may be configured to create a relatively uniform purse string effect when the suture 235 is engaged. Thus, in some embodiments, the uniformity of the purse string effect may be influenced by the proximity of the suture threading eyelets 236 to the proximal end 202 of the stent 200. In other embodiments, the uniformity of the purse string effect may instead, or also, be due to the elongated nature of the eyelets 236 which may allow a suture 235 to more readily slide through the eyelets 236 during tightening.

In some ways analogous to the eyelets 236 at the proximal end 202, the stent 200 may be configured with rounded elongate knobs 246 coupled to one or more apexes 215 of the scaffolding structure 210 at the distal end 204 of the stent 200. In some aspects these knobs 246 may resemble the shape of the eyelets 236 though there is no hole present in the knobs 246. Further, the knobs 246 may be larger or smaller than eyelets 236 on the same stent 200, depending on stent design parameters, such as the relative size and flare of the proximal 202 and distal 204 ends of the stent 200.

Similar to the eyelets, the elongated design of the knobs 246 may be configured to distribute the expansive force of a stent 200 acting on a body lumen when the stent 200 is deployed. This distribution of force, in connection with the smooth and rounded shape of the knobs 246, may be configured to lessen the trauma to body tissue which contacts the distal end 204 of the stent 200.

FIGS. 2A and 2B further illustrate a valve 250 coupled to the inside diameter of the stent 200. As shown in FIG. 2, the valve 250 may be located within the valve zone γ of a stent 200, and may be positioned closer to the distal end 204 of the stent 200 than to the proximal end 202.

The valve 250 may be coupled to the stent 200 by one or more rows of stitching 254 around the circumference of the stent 200. In other embodiments the valve 250 may alternatively or additionally be coupled to the stent 200 through use of an adhesive, through welding, through caulking, and through other attachment methods. For example, in some embodiments the valve 250 may be positioned with the stent 200 prior to applying a coating to the stent 200. Application of the coating may serve to simultaneously bond the valve to the coating in some instances.

Further, the stent 200 may be configured with one or more marker eyelets 248 coupled to the scaffolding structure 210 of the stent 200. In some embodiments there may be between 2 and 6 marker eyelets 248 around the circumference of the stent, including embodiments with about 4 total markers. A radiopaque tantalum (Ta) marker may be laser welded to one or more of these eyelets 248 in some embodiments. In other embodiments, any material which is visible for x-ray or fluoroscopic imaging may be used—for example, high density metals such as gold, platinum, tantalum, and so on. The marker may also or alternatively be riveted to the eyelets 248. A radiopaque marker may be utilized to position the stent 200 within the body of a patient in some instances. In some instances the marker eyelets 248 may be positioned at the same longitudinal location along the stent 200 as the proximal most edge of the valve 250.

FIGS. 2 and 2A also illustrate a suture 235 configured for use in connection with the stent 200. The suture 235 may be configured to allow a practitioner to engage the suture 235 in order to aid in removing and/or repositioning the stent. In some instances this may be accomplished by the practitioner grasping and displacing the suture 235 through use of a remote access tool, such as grasping forceps. The suture 235 may be formed of a metal, a thread, or any other material. In some embodiments, the suture 235 may comprise one or more radiopaque portions 238 for use in deploying, removing, or repositioning a stent. The radiopaque portions may be formed of a metal, such as gold, and enable a practitioner to distinguish these portions by x-ray or similar methods, thus allowing the practitioner to more easily capture suture 235 of a deployed stent with a remote capturing tool. Similarly, the suture 235 may also or alternatively comprise endoscopic markers, or markers visible through an endoscope, to aid a practitioner in viewing or manipulating the stent in connection with an endoscope. In some embodiments certain markers, such as markers comprised of gold, may be both radiopaque and visible through an endoscope.

Figure 3:
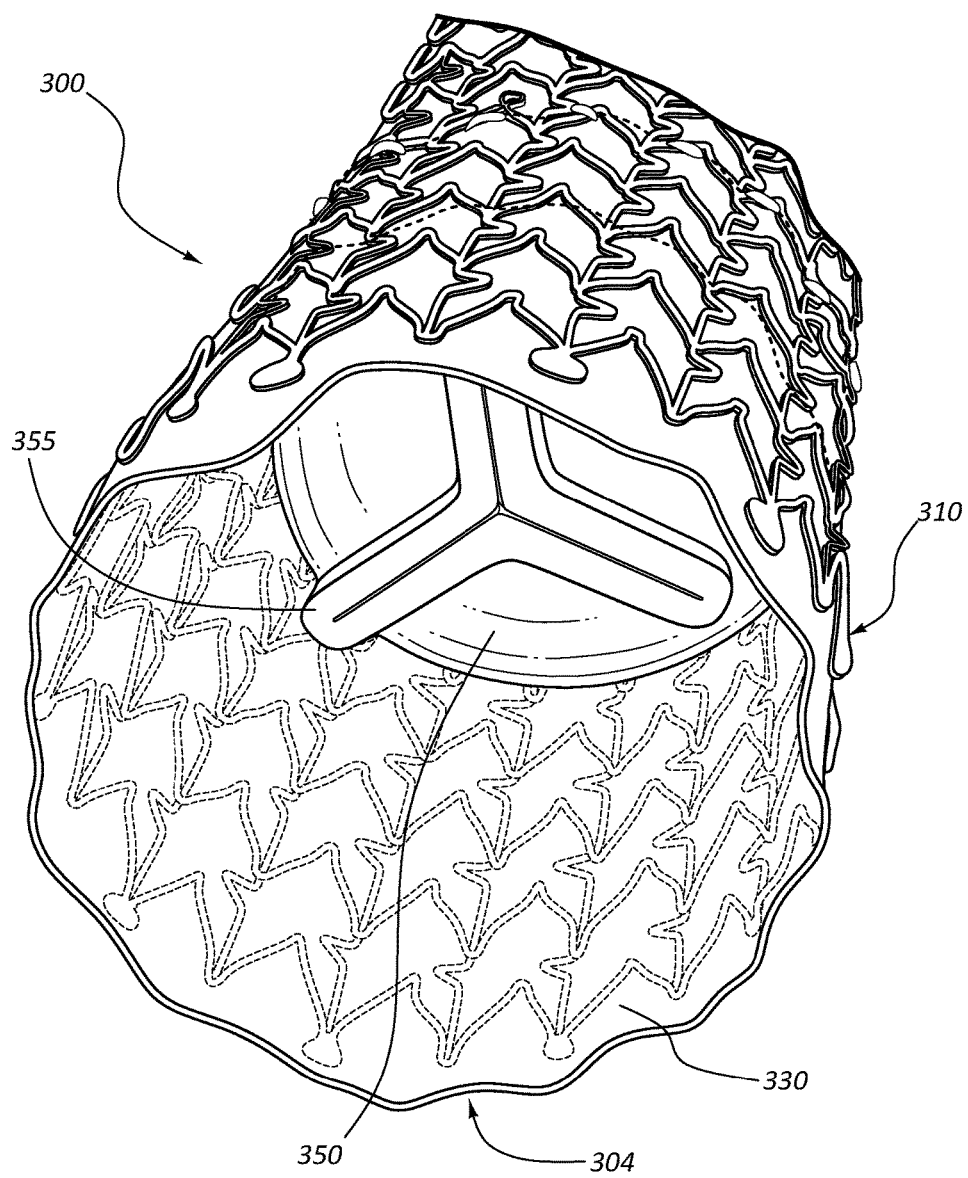
FIG. 3 is a partial perspective view of another embodiment of a stent.

FIG. 3 is a perspective view of a portion of a stent 300 including a valve 350. The stent 300 has a distal 304 end, a covering 330, and a scaffolding structure 310. The stent 300 is oriented such that the valve 350 is visible through the opening at the distal end 304 of the stent 300. In other embodiments, the valve 350 may be positioned at other locations along the longitudinal length of the stent 300, including locations closer to the proximal end (not shown) of the stent 300.

FIGS. 4A-4D are multiple views of a valve 450 configured for use with a stent. The valve 450 may be formed of an elastomeric or polymeric material and may comprise an upper surface 451, a lower surface 452, and a rim 453. The rim 453 may provide structure and support to the valve 450 as well as providing a location at which the valve 450 may be coupled to a stent, for example, by stitching.

Figure 4A:
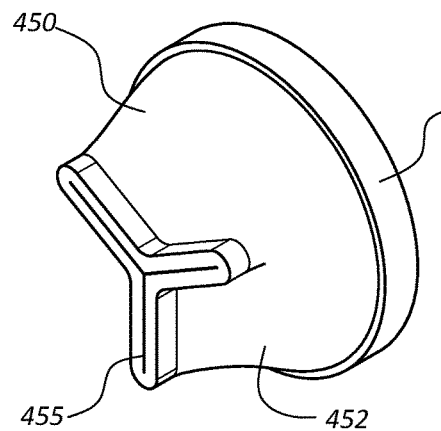
FIG. 4A is a perspective view of a valve for use with a stent.
Figure 4B:
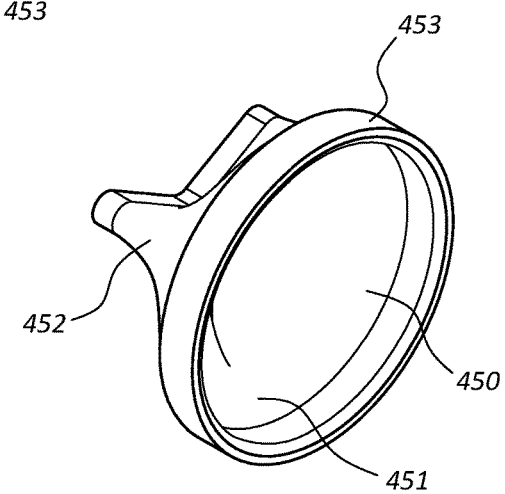
FIG. 4B is a second perspective view of the valve of FIG. 4A.
Figure 4C:
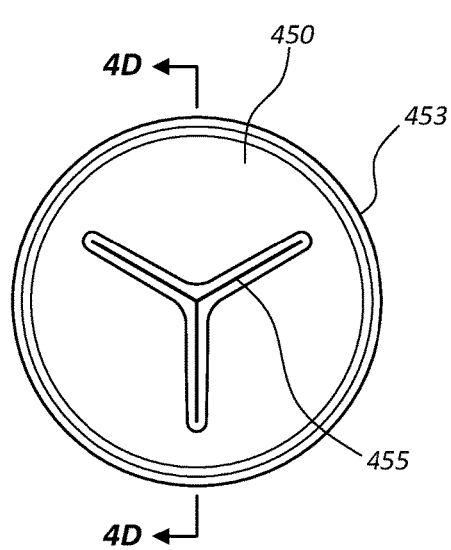
FIG. 4C is a top view of a the valve of FIG. 4A.
Figure 4D:
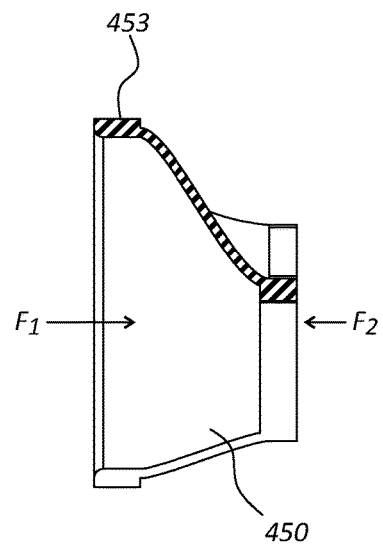
FIG. 4D is a cross-sectional view of the valve of FIG. 4C, taken through line 4D-4D.

The valve 450 may further comprise an opening 455 which is closed when the valve 450 is not actuated. In the illustrated embodiment, the valve opening 455 comprises three intersecting slits in the valve body. The valve opening 455 may be opened in response to a force acting on the upper surface 451 of the valve 450. Likewise, the valve may be opened by a force acting on the lower surface 452 of the valve 450. The shape and design of the valve 450 may be such that the force required to open the valve 450 by acting on the lower surface 452 is much larger than the force required to open the valve 450 by acting on the upper surface 451. For example, FIG. 4D illustrates two forces, $F_1$ acting on the upper surface 451 of the valve 450 and $F_2$ acting on the lower surface 452 of the valve 450. In response to $F_1$, the three-sided valve opening 455 may relatively easily open, as opposing sides of the opening 455 are pushed away from each other. Contrarily, in order for $F_2$ to open the valve 450, the entire lower surface 452 must deform, folding in on itself until the valve opening 455 is located on the opposite side of the rim 453. Thus, the valve 450 may be designed such that it is more easily opened in one direction than the other.

In the case of esophageal stents, a valve such as valve 450 may be positioned such that the lower surface 452 faces the stomach while the upper surface 451 faces the mouth. In this orientation, the valve 450 may more readily open to allow food to pass to the stomach, but generally will prevent reflux from the stomach, except in response to a relatively large force—for instance when a patient belches or vomits.

Notwithstanding the specific disclosure provided in connection with FIGS. 4A-4D, it is within the scope of the current disclosure to utilize a stent with any type or design of valve, or without a valve at all.

In some embodiments, stents may be crimped and packed within a catheter by a manufacturer, prior to shipping. In other embodiments, stents may be self-sheathing. As used herein, "self-sheathing" stents are stents configured to be at least partially sheathed by a user, either in the context of initially sheathing a stent (for example prior to deployment) or in the context of sheathing a deployed stent for repositioning or removal. Thus, in some embodiments, a stent may be configured such that the self-sheathing process does not deform or alter the stent in such as way as to limit the usability of the stent when subsequently deployed. In some embodiments, a self-sheathed stent may be configured such that a user may sheath the stent just prior to use. For embodiments which utilize a valve, a stent may be configured to be, at least partially, self-sheathing to avoid deforming the valve for an extended period of time. For example, a stent with a valve, such as valve 450, when crimped and packed in a catheter for an extended period of time, may kink, crease, or otherwise plastically deform. Thus, in some embodiments, a stent may be designed such that it is partially or fully self-sheathing, minimizing the time the valve is deformed within a catheter. Specifically, in some embodiments a stent may be designed such that a portion of the stent is crimped and loaded by a manufacturer, while the portion of the stent containing the valve is sheathed by the user just prior to use.

Referring back to FIGS. 1-1E, certain features of the stent 100 may be configured to allow the stent to be self-sheathing. Stent 100 may be configured such that a portion of the proximal zone α is crimped and sheathed within a catheter prior to use. Circumferentially aligned connectors along portions of the proximal α, transition β, and valve γ zones which are not pre-loaded into the catheter may be configured to provide axial strength to the stent 100, allowing the remainder of the stent to be pulled into a catheter by the user without the stent 100 deforming in the axial direction. A deployment device may be configured to anchor to the stent at one or more points along the stent wherein the connectors are circumferentially aligned. For example, stent 100, which has alternating connectors for the three proximal-most rows, may be configured to be anchored to the sheathing mechanism distal the third row of annular segments. In some embodiments, a stent 100 may have circumferentially aligned connectors along the entire length of the stent 100. In still other embodiments, all the connectors may be offset, or aligned in some zones and offset in other zones. In some instances, deployment devices may be utilized which are configured to grip the stent 100 at any point; aligned connectors may be optional in such embodiments.

Moreover, the relatively large number of connectors 120 within the valve zone γ may be configured to aid in self-sheathing. In particular, a large number of circumferentially aligned connectors may be configured to provide axial and radial strength and stability during self-sheathing. In some instances, the valve zone γ may be configured to uniformly contract during self-sheathing, thus applying balanced forces to the valve. In some instances this may mitigate potential deformation of the valve.

Similarly, the use of V-shaped connectors 120 within the valve zone may be configured to aid in self loading of the stent 100. V-shaped connectors may result in less friction between the stent and the catheter during self loading as the angled portion of one side of the V may more easily slide into a catheter than an omega-shaped connector where the catheter may become caught on the outwardly rounded portion of the omega shape.

Furthermore, the transition zone β may be configured such that the transition between the softer proximal zone α and the harder valve zone γ is not overly extreme; the transition zone β may be configured such that the axial and radial forces required for self-sheathing are uniformly transferred between the soft and hard zones of a stent. Furthermore, the transition zone β may be configured to provide uniform expansion between the proximal α and valve γ zones during deployment of the stent.

In the embodiment of FIG. 1, no anti-migration portions 128 are located within the valve zone γ or the transition zone β. Thus, in the illustrated embodiment, all anti-migration portions 128 may be crimped and loaded into the catheter by a manufacturer, minimizing the chance of the anti-migration portions catching on the edge of the catheter, or otherwise interfering with self-sheathing. In other embodiments anti-migration portions 128 may be positioned at any point along the stent 100, including portions that are configured for self-sheathing.

FIG. 5 is a side view of a stent 500 in an unexpanded state. More particularly, FIG. 5 is a side view of an unexpanded stent in a "rolled out" state, depicted as if the stent 500 were cut in the longitudinal direction and rolled out flat such that the entire circumference of the stent 500 may be viewed flat.

In some embodiments, a stent 500 may be formed by cutting a pattern, such as that shown in FIG. 5, into a tube of material. In some instances the material may be a memory alloy, and the cutting may be accomplished through use of a laser. The cut tube may then be stretched and expanded. The unexpanded stent of FIG. 5 has many similar features to the other stents discussed herein, though the other stents were depicted in expanded states.

As mentioned in connection with other embodiments, and as illustrated in FIG. 5, a stent 500 may be configured such that strut arms 514 toward the ends 502, 504 of the stent 500 may be longer than strut arms 514 disposed at or near the mid-body 503 of the stent 500.

In the illustrated embodiment, the stent 500 has twenty total rows of annular segments 512. As illustrated, the rows of annular segments 512 closest to either end are configured to comprise flared portions of an expanded stent. In the illustrated embodiment, the strut arms 514 near the ends 502, 504 of the stent 500 are relatively longer than the strut arms 514 located near the mid-body 503 of the stent 500. A wide variety of strut arm 514 lengths is within the scope of this disclosure. For example, in some instances the strut arm 514 lengths may vary along the length of the stent 500 from strut arm 514 lengths of about 4 mm to about 5.25 mm.

In the illustrated embodiment, the stent 500 is configured with about 20 pairs of strut arms 514 on each row around the circumference of the stent 500. The total number of strut arms 514 around the circumference may be influenced by the geometry of the stent 500; for example, the number of connectors, strut arm width, and size of the inside radii may all impact the total number of strut arms 514 which may be disposed about the circumference of the stent 500. Similarly, the desired angle of each apex may impact the number of strut arms 514 which may be disposed about the circumference of the stent 500. For example, for apex angles of about 30 degrees there may be between about 16 and about 24 pairs of strut arms 514 disposed about the circumference. For apex angles of about 60 degrees there may be between about 18 and about 22 pairs of strut arms 514 disposed about the circumference. In the illustrated embodiment, configured for apex angles of about 45 degrees, there are about 20 pairs of strut arms 514 about the circumference. In some embodiments any of these parameters, including the number of strut arms 514 and apex angle, may vary in different zones of the same stent 500.

In the illustrated embodiment the flare sections begin about 4 rows in on the proximal end 502 of the stent and about 5 rows in on the distal end 504 of the stent 500. In other embodiments the flare sections may be more or less than this, including embodiments where the flare sections are from about 2 rows to about 8 rows long including from about 4 rows to about 6 rows. In the illustrated embodiment, the relative length of the strut arms 514 gradually increases at the beginning of each flare section of the stent 500 moving toward either end 502, 504. For example, in one embodiment the lengths of the strut arms 514 may be about 4 mm at the beginning of each flare section, and gradually increase to about 5.25 mm near the proximal 502 or distal 504 ends of the stent 500. In other embodiments the strut arms 514 may likewise vary from about 4.25 mm to about 5.0 mm, or from about 4.5 mm to about 4.75 mm. In still other embodiments, the stent 500 may be designed such that the strut arm 514 lengths in a particular zone of the stent 500 are constant and gradually change in other zones. For instance, in some embodiments, a relatively long stent may be formed by forming a mid-body 503 section with a constant strut arm 514 length and gradually increasing the strut arm 514 length in flare sections adjacent the ends 502, 504 of the stent 500. Numerous stent lengths are within the scope of this disclosure, including, for example, stents from about 70 mm to about 150 mm in length, including stents from about 100 mm to about 120 mm in length.

Figure 5C:
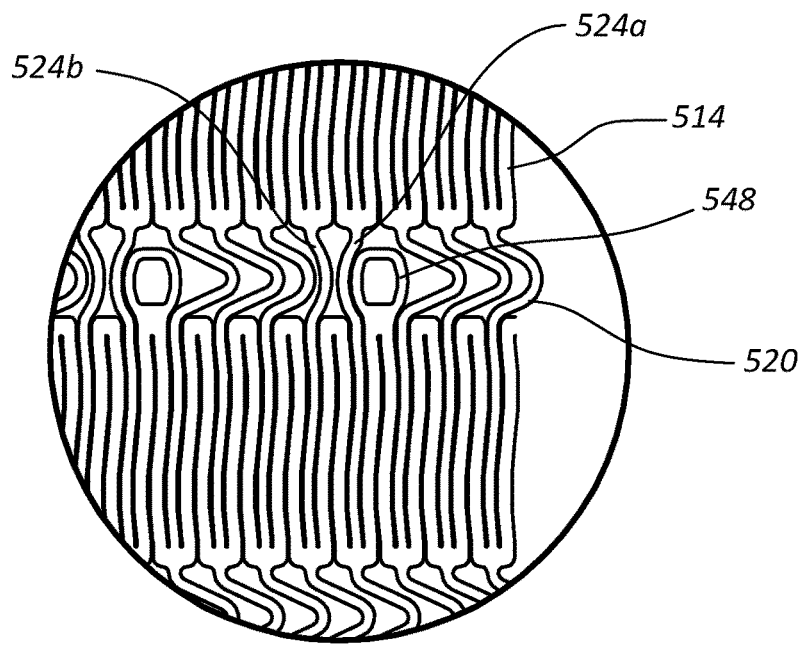
FIG. 5C is a third close up view of the stent of FIG. 5.
Figure 5D:
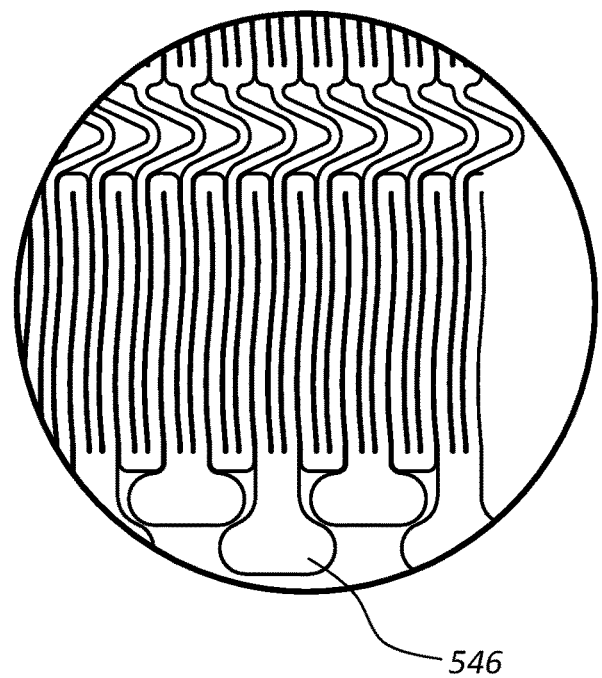
FIG. 5D is a fourth close up view of the stent of FIG. 5.

FIGS. 5A-5D are detailed views of portions of the unexpanded stent of FIG. 5. These figures show the relative position of the strut arms 514, suture threading eyelets 535, marker eyelets 548, connectors 520, and anti-migration portions 528 when the stent 500 is in an unexpanded state.

As shown in FIGS. 5 and 5A the relative size of the suture threading eyelets 535 may be related to the total number of eyelets and the diameter of the tube of material from which the stent 500 is cut. In some embodiments, the eyelets may be shaped with the maximum elongation in the circumferential direction allowed by the number of eyelets 535 and the circumference of the tube. Similarly, and referring also to FIG. 5D, in some embodiments the rounded elongate knobs 546 may be sized as large as possible given the diameter of the material from which the stent 500 is formed. Again referring to the illustrated embodiment, adjacent knobs 546 and/or eyelets 535 may be offset along the longitudinal direction in order to allow for relatively larger knobs 546 and/or eyelets 535. The illustrated embodiment has knobs 546 and eyelets 535 at two longitudinal positions; in other embodiments the knobs 546 and/or eyelets 535 may all be in-line or may be disposed at more than two longitudinal positions. In some instances the stent 500 may be formed from a tube of material having a diameter from about 3 mm to about 8 mm, including from about 4 mm to about 6 mm or about 5 mm.

FIG. 5C is a close up view of a portion the stent of FIG. 5, showing one possible relationship between a marker eyelet 548 and surrounding connectors 520 in an unexpanded state. In the illustrated embodiment, the second portion of certain connectors near the marker eyelet 548 may have a less pronounced shape due to the use of material for the marker eyelet during the cutting process. For example, second portions 524a and 524b are straighter, having less of a V-shape, than surrounding connectors, thus allowing for more material to be used to form the marker eyelet.

Numerous sizes and configurations of stents are within the scope of this disclosure. By way of example, and not limitation, in addition to esophageal stents, the current disclosure is also applicable to biliary stents and other stents which may utilize a valve. In some embodiments this disclosure may be used with such stents in the following sizes and dimensions. Biliary stents: mid-body diameters from about 6 mm to about 11 mm including diameters of about 8 mm to about 10 mm; flare sections configured to expand from about 0.5 mm to about 2 mm in diameter greater than the mid-body diameter of the stent; and lengths of from about 40 mm to about 100 mm, including lengths from about 60 mm to about 80 mm.

Figure 6:
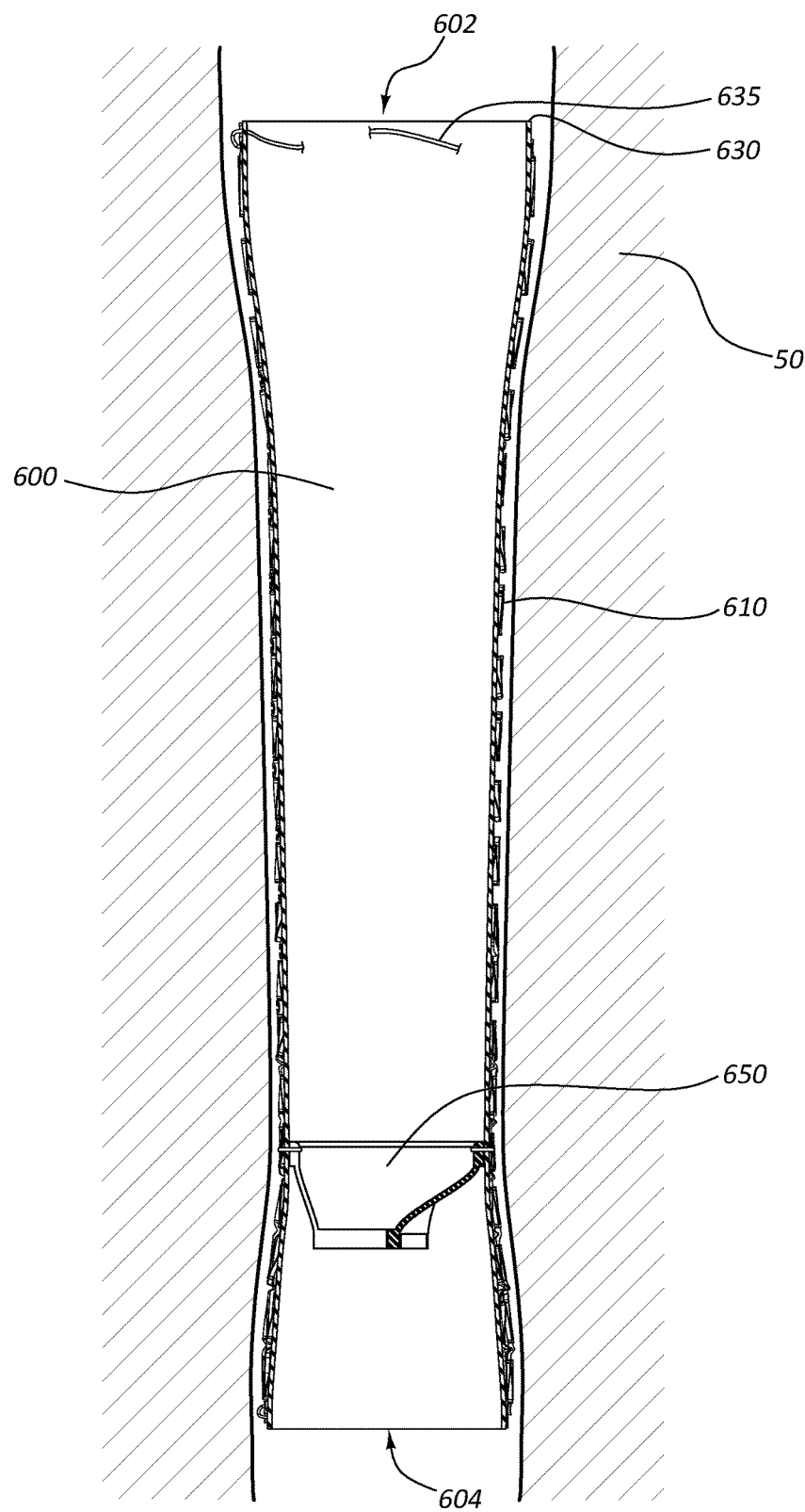
FIG. 6 is a cross-sectional view of a stent disposed within a body lumen.

FIG. 6 is a cross-sectional view of a stent 600 deployed within a body lumen 50. The stent comprises a scaffolding structure 610, a covering 630, a suture 635, and a valve 650.

In some instances the body lumen 50 may be the esophagus. In these instances, a variety of stent placements are possible, including placements where a portion of the stent 600 at the distal end 604 extends into the stomach. In some instances, for example, the valve 650 may be aligned with the lower esophageal sphincter and the distal end 604 of the stent 600 positioned within the stomach. In other embodiments, the valve 650 may be aligned with the lower esophageal sphincter with the distal end 604 of the stent 600 located proximal to the stomach or flush with the stomach.

The examples and embodiments disclosed herein are to be construed as merely illustrative and exemplary, and not a limitation of the scope of the present disclosure in any way. It will be apparent to those having skill with the aid of the present disclosure in the art that changes may be made to the details of the above-described embodiments without departing from the underlying principles of the disclosure herein. It is intended that the scope of the invention be defined by the claims appended hereto and their equivalents.

The invention claimed is:

1. An implantable device having a generally cylindrical shape, configured to be disposed within a body lumen, the device comprising:
    a scaffolding of struts, comprising:
        a plurality of annular segments disposed along the circumference of the cylindrical shape, the segments arranged in rows in the longitudinal direction of the cylindrical shape, each annular segment comprising a plurality of interconnected arms;
        a plurality of connectors extending between and interconnecting adjacent annular segments;
        wherein the annular segments and connectors of the implantable device define a proximal zone adjacent to and extending from a first longitudinal end of the cylindrical shape, a valve zone adjacent to and extending from a second longitudinal end of the cylindrical shape, and a transition zone located between the valve zone and the proximal zone, each zone comprising a plurality of annular segments, wherein the transition zone is more compressible in a transverse direction than the valve zone, and wherein the proximal zone is more compressible in the transverse direction than the transition zone; and
    a valve coupled to an inside diameter of the cylindrical shape, the valve disposed within the valve zone.

2. The implantable device of claim 1, wherein adjacent arms of the plurality of interconnected arms are arranged at acute angles relative to each other.

3. The implantable device of claim 1, further comprising a plurality of eyelets, elongated in a circumferential direction of the cylindrical shape, the eyelets configured to receive a suture, and the eyelets disposed adjacent a first longitudinal end of the cylindrical shape.

4. The implantable device of claim 1, further comprising a polymeric cover coupled to the scaffolding of struts.

5. The implantable device of claim 1, further comprising a plurality of rounded knobs, the knobs elongated in a circumferential direction of the cylindrical shape, and the knobs disposed adjacent a second longitudinal end of the cylindrical shape.

6. The implantable device of claim 1, wherein a plurality of arms is curved and has an inflection point.

7. The implantable device of claim 1, wherein one or more connectors comprise an omega-shaped portion.

8. The implantable device of claim 7, wherein one or more connectors comprise a V-shaped portion.

9. The implantable device of claim 1, wherein one or more connectors within the valve zone comprise a V-shaped portion.

10. The implantable device of claim 1, wherein the device is configured with a greater number of connectors per row of annular segments in the valve zone compared to the transition zone, and a greater number of connectors per row of annular segments in the transition zone compared to the proximal zone.

11. The implantable device of claim 10, wherein two or more adjacent rows of connectors within each zone are circumferentially aligned.

12. The implantable device of claim 11, wherein a plurality of rows of connectors within the proximal zone are circumferentially aligned with connectors disposed in adjacent rows and one or more rows of connectors within the proximal zone are not circumferentially aligned with one or more adjacent rows of connectors.

13. The implantable device of claim 1, wherein a plurality of annular segments is configured to reduce in diameter in response to an axial force applied to the implantable device.

14. The implantable device of claim 1, wherein the device has a longitudinal length from 70 mm to 150 mm.

15. The implantable device of claim 1, wherein the device has a mid-body diameter of from 12 mm to 25 mm.

16. The implantable device of claim 1, wherein the angles at which adjacent interconnected arms are joined in the proximal zone are larger than the angles at which adjacent interconnected arms are joined in the transition zone, and wherein the angles at which adjacent interconnected arms are joined in the transition zone are larger than the angles at which adjacent interconnected arms are joined in the valve zone.

17. The implantable device of claim 1, wherein annular segments of the proximal zone have fewer interconnected arms than annular segments of the transition zone, and wherein annular segments of the transition zone have fewer interconnected arms than annular segments of the valve zone.

18. The implantable device of claim 1, wherein adjacent annular segments of the proximal zone are interconnected with fewer connectors of the plurality of connectors than adjacent annular segments of the transition zone, and wherein adjacent annular segments of the transition zone are interconnected with fewer connectors of the plurality of connectors than adjacent annular segments of the valve zone.

19. The implantable device of claim 1, wherein one or more connectors disposed in the proximal zone have a first shape and one or more connectors disposed in the transition zone have a second shape that is different from the first shape, and wherein one or more connectors of the valve zone have a third shape that is different from both of the first shape and second shape.

20. An implantable device comprising:
    a scaffolding of struts disposed between a first longitudinal end of the implantable device and a second longitudinal end of the implantable device,
    the scaffolding of struts defining a proximal zone adjacent to and extending from the first longitudinal end of the implantable device, a valve zone adjacent to and extending from the second longitudinal end of the implantable device, and a transition zone located between the valve zone and the proximal zone, wherein the transition zone is more compressible in a transverse direction than the valve zone, and wherein the proximal zone is more compressible in the transverse direction than the transition zone, and
    a valve coupled to an inside portion of the implantable device, the valve disposed within the valve zone.

* * * * *